United States Patent [19]

Linkow

[11] Patent Number: 4,682,951
[45] Date of Patent: Jul. 28, 1987

[54] ADJUSTABLE SINUS LIFT IMPLANT

[76] Inventor: Leonard I. Linkow, 1530 Palisade Ave., Fort Lee, N.J. 07024

[21] Appl. No.: 868,121

[22] Filed: May 28, 1986

[51] Int. Cl.⁴ ............................................. A61C 8/00
[52] U.S. Cl. .................................... 433/173; 433/176
[58] Field of Search ................ 433/173, 174, 175, 176

[56] References Cited

U.S. PATENT DOCUMENTS 4,187,609  2/1980  Edelman ............................. 433/176
4,431,416  2/1984  Niznick .............................. 433/174
4,522,596  6/1985  Ashkinazy .......................... 433/176

Primary Examiner—Robert Peshock
Attorney, Agent, or Firm—Darby & Darby

[57] ABSTRACT

An oral implant, and method of using it, allow for the permanent installation of an artificial tooth in an area of the maxilla adjacent a descendent portion of the maxillary sinus. An opening is made in the maxilla to the Schneiderian membrane at the floor of the sinus. The implant has a basket or cradle which is filled with bone chips and inserted into the opening. A base attached to the cradle by an adjusting shaft is positioned in the opening after the cradle, e.g., in grooves at anterior and posterior portions of the opening. The shaft is then used to set the spacing between the cradle and the base such that the Schneiderian membrane is lifted and the sinus is reduced. After a period of time, new bone grows into the groove and about the bone chips so as to fuse the implant in place and thicken the maxilla in that area. Then a post is fastened to the implant and is used to support an artificial tooth structure.

22 Claims, 15 Drawing Figures

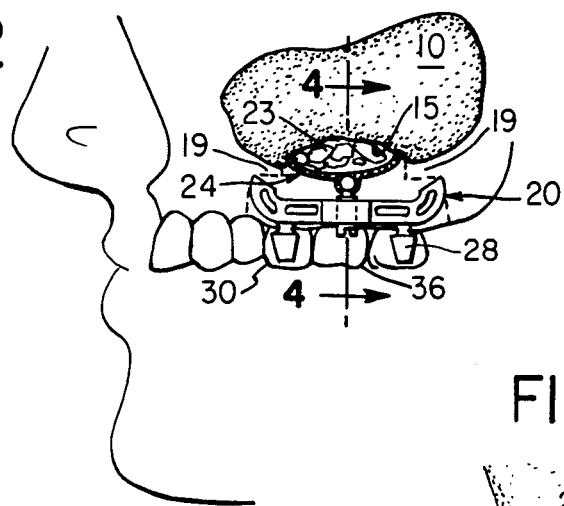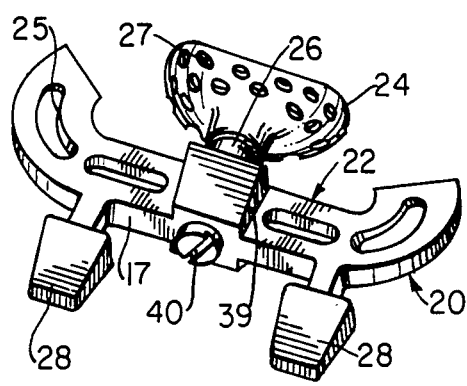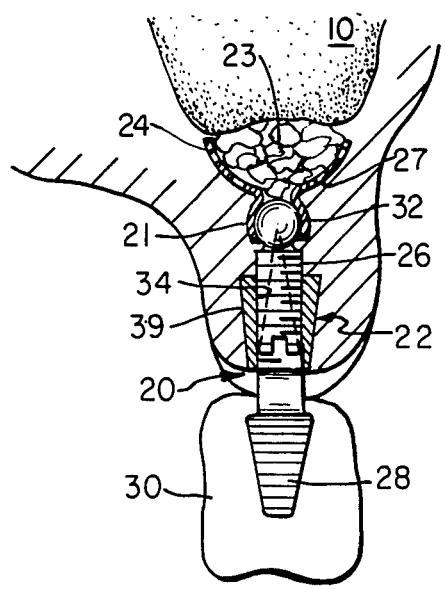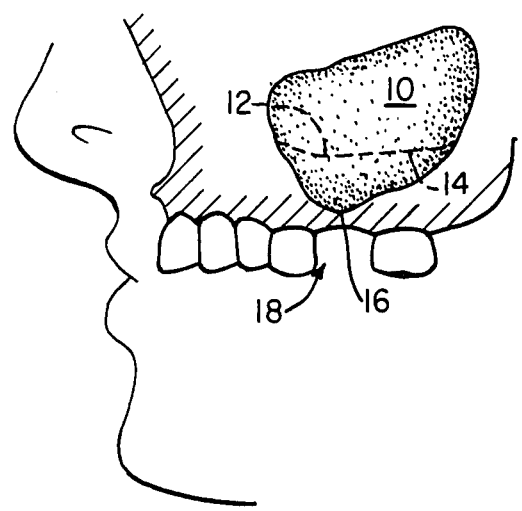

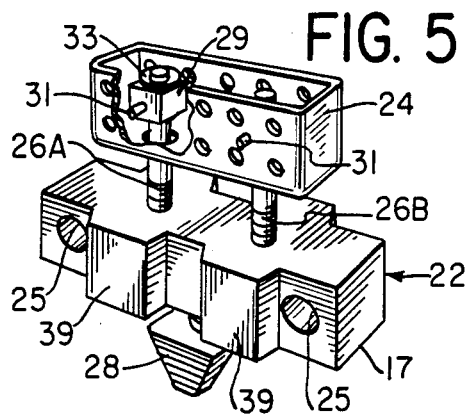
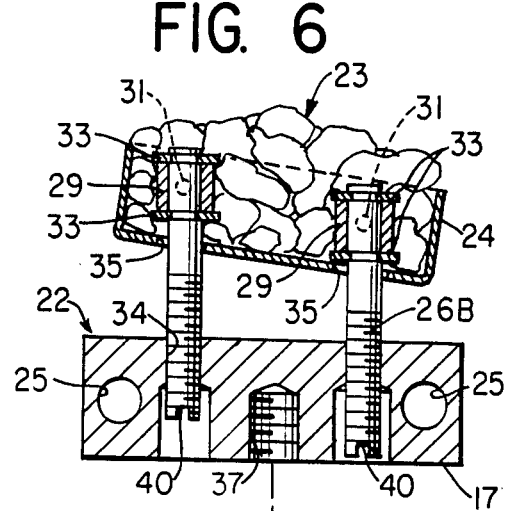
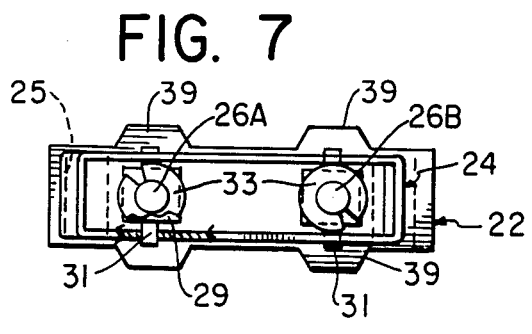
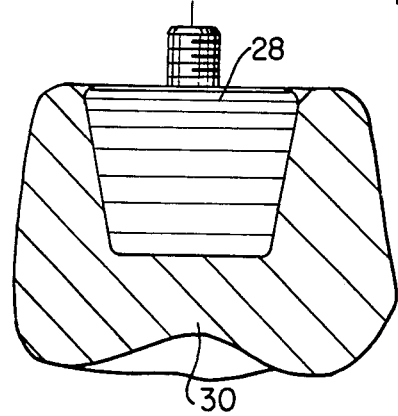
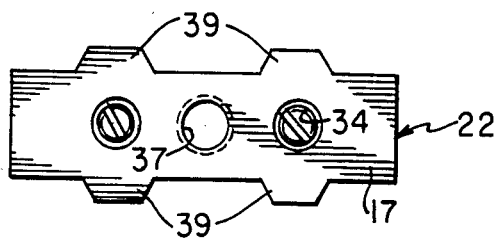
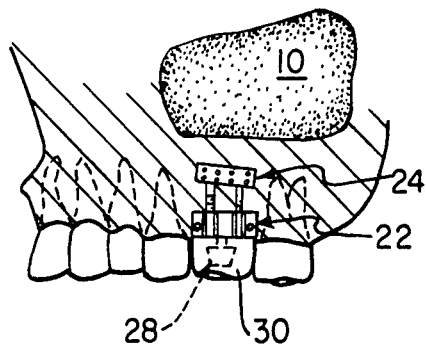

ADJUSTABLE SINUS LIFT IMPLANT

BACKGROUND OF INVENTION

The present invention relates to oral implants and, more particularly, to maxillary oral implants for use in patients who have enlarged sinus cavities.

The maxillary sinuses of a person are located on each side of the maxilla between the canine eminence and the tuberosity. The lowest point of the sinus floor usually lies superior to the first molar and the second premolar. However, the maxillary sinus shape varies greatly from one side of a person's face to the other, and from individual to individual.

As a person ages, the maxillary sinuses grow at the expense of the bone. Also, disease may cause resorption of bone. When bone loss occurs between the sinus floor and the dental arch, the feasibility of using maxillary dental implants is decreased.

Dental or oral implants are blades or screws with attached posts. These implants are surgically implanted in a patient's mandibule or maxilla along the occlusal plane. The implantation is achieved by exposing the bone with an incision through the gum tissue and creating a groove in the bone with a burr or drill. The implant blade is then wedged into the groove so that the post protrudes. Then the tissue is sutured about the bone and the base of the post. Finally, the post is used to mount an artificial dental appliance, such as a bridge.

A patient with an enlarged maxillary sinus has little bone in the maxilliary dental arch for accomodating the insertion of an implant. Consequently, the implantation procedure may result in the penetration of both the Schneiderian membrane on the sinus floor and the sinus itself. This may promote sinus infection and may result in the implant being only loosely held in the remaining bone, so that it fails to function effectively as a support for artificial teeth.

In U.S. Pat. No. 4,521,192 of the present inventor, there is suggested a technique for lifting the Schneiderian membrane and locating bone fragments beneath it in order to thicken the bone at the sinus floor by regrowth of new bone around the inserted the bone fragments. According to this suggestion, an implant is used which has a basket or cradle built into the blade portion. This basket is open toward the groove in the patient's bone and is filled with bone chips or fragments. Consequently, when the blade is wedged in the groove, the basket is moved to the base of the groove which, if the Schneiderian membrane is exposed, pushes the membrane upward into the maxillary sinus cavity.

The depth at which the blade of an implant is located in the patient's bone cannot be varied to any great extent with this prior apparatus. Thus, with this prior device, in which the basket is fixed to the blade portion of the implant, there is little control over the degree to which the Schneiderian membrane is lifted. This limits the oral surgeon's ability to increase the thickness of bone at the floor of the sinus cavity and to make it suitable for the retention of the implant.

SUMMARY OF THE INVENTION

The present invention is directed to an apparatus and method for installing oral implants in the maxilla of a patient in which the bone of the dental arch in an edentulous span is thin because of a descending maxillary sinus. This implant is made possible through the use of a bone chip container which is adjustably secured to the implant so that the maxillary sinus floor can be augmented with new bone in a desired configuration.

In an illustrative embodiment of the invention, the thin bone in an edentulous area of the dental arch of the maxilla is exposed. A groove is made in the bone mesial and distal to the floor of the sinus, and up to the Schneiderian membrane, which membrane lies on the floor of the maxillary sinus. In addition a larger opening is made through the bone toward the center of the groove. Then an especially designed sinus lift implant is installed in the groove.

The sinus lift implant has a container which is open at one side such that it is in the form of a cradle or basket. The basket has a size such that it can pass through the opening at the center of the groove made in the bone. Threaded apertures are located in the bottom of the basket of the blade and threaded shafts engage these apertures. The blade or base portion of the implant is narrow, at least at its ends, so that it can be wedged tightly in a portion of the groove in the bone at such a depth such that the base does not extend downwardly from the maxilla beyond the existing bone of the dental arch. One or more posts project downwardly from the base and can be used to mount an artificial tooth structure from the maxilla.

During installation, the open basket is filled with bone chips, either natural or artificial. Then the basket is passed up into the large opening in the maxilla below the Schneiderian membrane. The blade portions (mesial and distal) to the basket are then tapped into place so that the implant is wedged in the groove and the basket is at least flush with the alveolar crest. Access to the ends of the threaded shafts are provided through the bottom of the apertures in the base so that the shafts can be rotated. Rotation of these shafts raises, lowers or tilts the basket to redefine the shape and thickness of the sinus floor. The basket is then moved high into the maxillary sinus, although still below the Schneiderian membrane. Its base is now well above the alveolar crest so that it is easy to suture close the tissues beneath it.

Once in position, the gum tissue is sutured closed over the base portion. During a period of several weeks or months, new bone will grow and fuse with the surrounding bone and chips. This results in a thicker bone area enclosing the implant and a reduction in the size of the sinus. After the formation of the new bone, the artificial tooth structure is mounted on the post of the implant, which post protrudes beyond the gum tissue.

The posts themselves can be made independently from the implant itself, thus allowing the implant to be completely submerged during the healing process.

BRIEF DESCRIPTION OF THE DRAWINGS

The foregoing and other features of the present invention will be more readily apparent from the following detailed description and drawings of illustrative embodiments of the invention in which:

FIG. 1 is a schematic side view of a patients face showing the maxillary dental arch and a desended maxillary sinus;

FIG. 2 is an enlarged view of FIG. 1, showing one embodiment of an implant according to the present invention, which implant is partially in section and is shown installed in the patient's dental arch;

FIG. 3 is a perspective view of the implant according to FIG. 2;

FIG. 4 is a cross-sectional view of the arrangement of FIG. 2 along lines 4—4;

FIG. 5 is a perspective view, partly broken, of another embodiment of an implant according to the present invention;

FIG. 6 is a longitudinal sectional view of the implant of FIG. 5 along lines 6—6 and showing a basket portion in a tilted position;

FIG. 7 is a top view of the embodiment FIG. 5.

FIG. 8 is a bottom view of the embodiment of FIG. 5; and

FIGS. 9A-9G are schematic side views of a patient's face showing an implant installation process according to the present invention.

DESCRIPTION OF ILLUSTRATIVE EMBODIMENTS

Figure 9A:
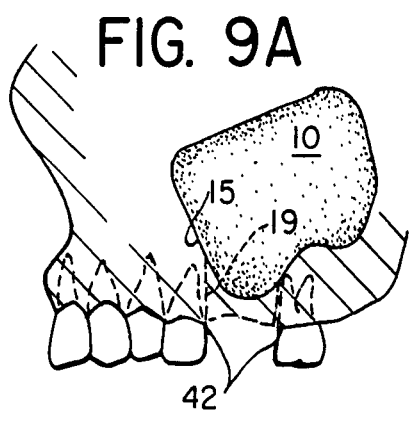

In FIG. 1 there is shown a side view in schematic form of patient's face. The shaded portion of FIG. 1 illustrates the upper bony structure of the face, including the maxilla, from which several teeth project dowardly. This bony structure defines the maxillary sinus 10 of the patient, which sinus has a floor 12 that has desended below its optimal position representated by dotted line 14. As a result, there is a low point 16 of the sinus floor 12 adjacent an edentulous span 18 of the dental arch. The desent of the sinus floor, and the expansion of the sinus itself, may be due to the aging process or to disease.

One way of filling the edentulous span with an artificial tooth or bridge involves implanting a device in the bone at the site of the edentulous span. A projection or post extending from this implant is then used to mount the artificial tooth or bridge. However, when the sinus has desended as far as shown in FIG. 1, the portion of bone between the ridge crest and the sinus is so thin that it does not provide sufficient support for the implant. The present invention corrects this by utilizing the implant procedure to thicken that bone and to shrink the sinus cavity, while anchoring the implant structure in place.

The result of the utilization of the present invention is illustrated in FIG. 2. In FIG. 2 an implant device 20 is shown positioned within a groove 19 (shown in dotted line) which is cut through the maxilla to the Schneiderian membrane 15, which lies along the floor of the sinus. The implant includes a blade or base portion 22 which is connected to a basket portion 24 by a single threaded shaft 26. Bone chips 23 are located in the basket 24 and cause the Schneiderian membrane 15 to be raised. The bone chips 23, as well as fenstrations 25, 27 (FIG. 3) in the implant base and basket, respectively, promote the growth of new bone around and through the implant. This new bone thickens the bone in the area of the implant and shrinks the sinus cavity.

Projecting downwardly from the base 22 is one or more posts 28 (shown in dotted line in FIG. 2) upon which an artificial tooth structure can be mounted. This structure may be one or more individual artificial teeth 30 or a support for a bridge 36.

The threaded shaft 26 passes into an aperture 34 in base portion 22 (FIG. 4). This aperture extends completely through the base portion so that the end 40 of the shaft 26 can be reached from the bottom. By turning the threaded shaft, via a slot in end 40, the separation between the base, which is wedged in the remaining bone, and the basket, which contains the bone chips, can be set so that the sinus cavity is reduced a desired amount and the area for regrowth of new bone is sufficient to anchor the implant in place.

An enlarged perspective view of the implant of FIG. 2 is shown in FIG. 3, and an enlarged cross section is shown in FIG. 4. The blade portion 22 is shown to have a shallow "U" shape. This design allows the ends of the blade portion to penetrate far into the available bone, while avoiding the lowest portions of the sinus cavity. Other shapes can be selected which fit the patient's bone structure. In addition the blade has an enlarged portion 39 which contains the threaded aperture 38 that receives threaded shaft 26. The slot at the end of the shaft will accomodate a screw driver or similar tool so that the shaft may be rotated.

As best seen in FIG. 4, the threaded shaft 26 has a ball 32 at the opposite end from the slot. This ball is rotatably received in a socket 21 of basket 24. Consequently, shaft 26 can be rotated without rotation of basket 24 and the basket can be tilted. As a result, the basket can be moved up into the sinus region under the influence of shaft 26, and can be set at an angle to produce the desired slope for the sinus floor.

During insertion of an implant, such as that in FIG. 3, into the maxilla of a patient, the bone along the dental arch is exposed and a burr is used to form a groove in the bone, which groove is about the size of the blade portion and is deep enough to bury the blade in the groove so the lower surface 17 of the blade portion is completely within bone. In the middle of this groove, additional bone may be removed such that basket, which is somewhat wider than the blade, can pass into the bone. At this point, the bone is removed all way to the Schneiderian membrane. As a result, the ends of blade portion can be wedged in bone on both sides of a larger aperture in the bone through which the basket may easily pass.

In FIG. 5, there is shown a perspective view of a modified version of the implant of FIGS. 2-4. The principle difference between the implant of FIG. 5 and that in FIG. 2 is that the implant of FIG. 5 contains two threaded shafts, 26A and 26B. These threaded shafts are received in pivotable threaded blocks 29 located within the basket. As a result, not only can the separation between the base or blade portion 22 and the basket 24 be controlled, the basket can be tilted to give the floor of the sinus cavity a particular shape or slant as desired by the oral surgeon. The tilting of the basket with respect to the base is best shown in FIG. 6, which is a cross-sectional view of the implant of FIG. 3 along lines 6—6.

The second embodiment also uses a qenerally rectangular blade or base portion, as opposed to the shallow "U" shape. This illustrates that the base portion may have any convenient overall shape which allows it to best utilize the bone structure available and to avoid contact with the sinus cavity.

In FIG. 6, the basket 24 is shown filled with artificial or natural bone chips 23 as in the first embodiment. Connected to the sides of the basket 24 are axles 31 of threaded blocks 29. The axle 31 are best shown in FIG. 5. Because the axles 31 are received in holes in the sides of the basket 24, the threaded blocks 29 can pivot with respect to the basket 24. Thus, if it is desired to create a sloped floor to the sinus cavity, one of the threaded shafts 26A can be screwed out further than the other shaft 26B. This causes the basket to tilt, as shown in FIG. 6. However, to keep the shaft from binding within the basket, the threaded blocks 29 pivot with respect to the basket. The shafts are prevented from pulling out of the blocks by means of snap washers 33 located on the shafts above and below the blocks. Other suitable means could also be used for retaining the shaft within the pivoting blocks in the basket, while still allowing the shafts 26 to rotate.

As a means of accommodating the tilting of the basket, large openings 35 are provided in the lower portion of the basket where the shafts 26 penetrate. As a result, the shafts do not hit against the basket bottom when it is titled.

When the implant is first inserted in the patient's maxilla, the surrounding bone may not be sufficiently strong to place the implant into operation. In particular, if a patient were to have an artificial tooth mounted on the implant and were to begin chewing on food, there is a danger that the surrounding bone will fracture. Thus, sufficient time must be allowed for new bone to grow in and about implant. To make sure that, while new bone is growing, the implant is not dislodged by the patient's tongue or other teeth during the chewing process, the implant may be in the form of a submergible implant, i.e. an implant with a detachable post. With such an implant the base portion is positioned in the groove in the maxilla so that bone can grow completely over its lowermost surface 17. Once bone regrowth has occurred, a portion of the base having a threaded aperture 37 is then exposed and the post 28 is inserted. Such an arrangement is shown in FIG. 6, where the post 28 with an artificial tooth 30 mounted thereon, is shown to be attachable by screw threads to the aperture 37 at the bottom surface 17 of the base member 22. Other forms of submergible implants and means for connecting posts thereto are disclosed in the present inventor's pending U.S. patent application Ser. No. 582,935 filed Feb. 23, 1984 and entitled "Submergible Blade Implant". This application is hereby incorporated by reference.

FIG. 7 shows a top view of the implant of FIG. 5. It can be seen from this view that the basket and the implant base are approximately the same width. However, the implant base is made slightly larger, or has lateral projections 39, such that the implant base can be wedged against the sides of the grooves formed in the patient's bone, while the basket can pass through the groove without substantial obstruction. This is a variation of the arrangement in FIG. 2 wherein the basket is wider than the base and the groove must be widened at the location of the basket.

Once the implant is in place in the patient's bone, adjustment of shafts 26 is achieved by rotating the shafts. The ends 40 of these shafts have recesses or slots which can be engaged by a small screw driver. These recesses can be reached from the bottom 17 of the base 22 through apertures 34 in which the shafts are threaded. Thus by passing a screw driver up into aperture 34, the shafts 26 can be reached and rotated to cause the basket to move away from the base portion and/or assume a tilted position.

The procedure for inserting the implant and shrinking the sinus cavity is set forth in a step-by-step manner in FIGS. 9A-9G which illustrate the upper facial bone of the patient. In FIG. 9A, an incision is shown in the patient's gum tissue along the dental arch in an endentulous span. The muco- periosteal tissue 42 is then reflected to expose the underlying bone, mesial and distal to near sinus exposure. If the Schneiderian membrane is not exposed by reflecting the tissue because of the presence of bone, this bone is carefully removed with a large round burr so as to form an opening 19 in the bone below the sinus membrane. The opening may be in the form of a larger central opening that is large enough to allow the basket 24 to pass through, and grooves on each side of the central opening that are small enough to cause the base 22 to become wedged therein at a depth such that its lower surface 17 is above the lower bone rim of the maxilla. With the embodiment of FIG. 2, this is accomplished by first forming a groove for the base and then expanding the groove in the center where the basket 24 is positioned.

Figure 9B:
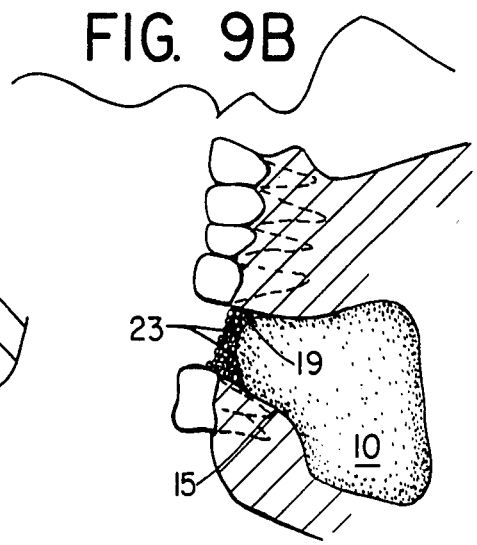

If desired, the patient may be placed in a reclining position with his head back so that a desired amount of bone fragments 23 can be inserted into the opening such that they rest against the Schneiderian membrane 15. The amount of bone material which is placed in the opening will depend on the amount by which the sinus cavity is to be reduced. This step is shown in FIG. 9B.

Figure 9C:
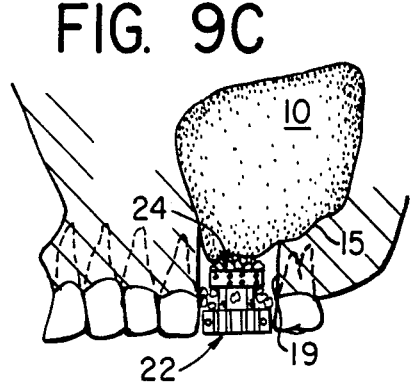

The next step involves filling the cradle or basket 24 with bone chips and inserting it at least part the way into the widened opening 19. At this point, if the basket 22 is separated from the base 22, additional bone fragments can be placed between these two parts as shown in FIG. 9C.

Figure 9D:
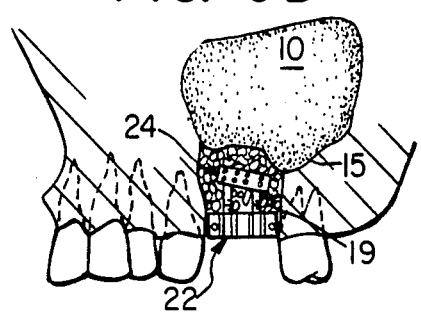
Figure 9E:
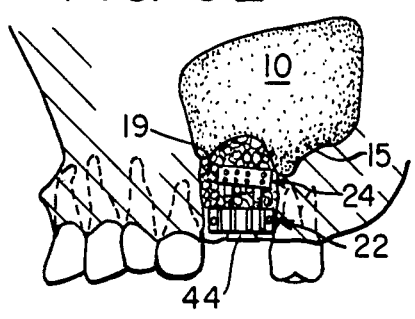
Figure 9F:
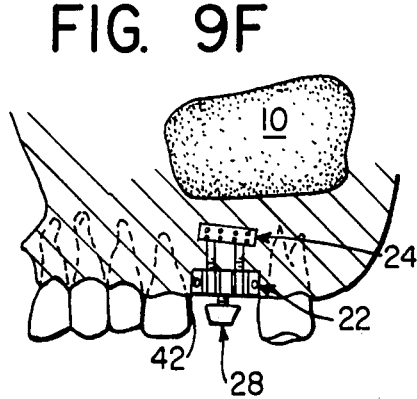

The implant base is then pushed into the grooves at the ends of the opening and is gently tapped into place, for example, with a mallet, such that it becomes snugly wedged in those grooves, as shown in FIG. 9D. If a submergible implant base is used, the mucoperiosteal tissue is then resutured over the implant. It is desirable however, to insert a plastic cap 44 into the aperture 37 so that the growth of new bone does not block this aperture. Thus, in FIG. 9E the tissue 42 is shown sutured over the cap 44.

A period of several weeks to several months is allowed to pass. During this time, the oral surgeon can check the growth of the new bone by X-ray techniques. This new bone will fuse with the bone chips placed in the groove 19, and will also penetrate the fenstrations located in the base and basket of the implant. Eventually a solid mass of bone will form about the implant, firmly anchoring it in place and reducing the sinus cavity permanently.

Synthetic non-resorbable hydroxyappatite can also be used in the basket and below the Schneiderian membrane in place of natural bone. In such situations, no new bone will grow, but the synthetic non-resorbable particles that remain the underlying basket will serve to push up the sinus membrane and keep it away from the oral cavity environment.

After the implant is firmly anchored in fused bone, the tissue 42 is again opened and the cap 44 is removed. Then the post 28 is inserted in the aperture 37, and an artificial tooth or similar structure is attached to the post, for example by cement. The tissue 42 is resutured about the neck of the post, as shown in FIG. 9G.

The present invention allows an implant to be used in an area in which there would otherwise be too little bone. In fact, it increases the bone in the area itself. Further, it allows the shape of the floor of the sinus cavity to be regulated by tilting the basket 24 at any desired angle.

While the invention has been be particularly shown and described with reference to preferred embodiments thereof, it will be understood by those skilled in the art that various changes in form and details may be made therein without departing from the spirit and scope of the invention.

I claim:

1. An oral implant for implanting an artifical tooth supporting structure in an opening created entirely within an edentulous span of the dental arch of the maxilla of a patient, such that the opening leaves sufficient bone to support said implant prior to being put in operation, comprising:
  a basket-like container portion open at one side, said container portion having a size such that it can be passed easily into the opening;
  a base portion having a size such that it can be wedged tightly in a portion of the opening in the bone; and
  adjusting means for adjusting the distance between said container portion and base portion.

2. An oral implant as claimed in claim 1 wherein the adjusting means is at least one shaft projecting from one side of said base portion, said shaft connecting said base portion to another side of said container portion which is opposite the open side, said shaft being rotatable and in threaded engagement with one of said container portion and base portion such that rotation of the shaft adjusts the distance.

3. An oral implant as claimed in claim 1 wherein said container portion and base portion have fenestrations which promote bone growth through the implant.

4. An oral implant as claimed in claim 1 wherein the container portion is adapted to hold bone chips.

5. An oral implant as claimed in claim 1 wherein the part of the opening in which the container is located extends completely through the maxilla of the patient to Schneiderian membrane at the floor of the patient's maxillary sinus, the container portion is adapted to hold bone chips, and the container portion is adapted to pass completely through the opening such that the bone chips are brought into contact with the Schneiderian membrane.

6. An oral implant as claimed in claim 15 wherein said post is detachably connected to said base.

7. An oral implant as claimed in claim 6 wherein a section of said post has a threaded shaft and the other side of the base defines a matching threaded aperture, said post being threadably received in the aperture.

8. An oral implant as claimed in claim 2 wherein said container portion is connected to said shaft by a ball and socket joint.

9. An oral implant as claimed in claim 1 wherein the opening has a narrower groove for a portion thereof and said base portion is adapted to be wedged in the groove at a depth such that no part of it extends out of the groove.

10. An oral implant as claimed in claim 13 further including at least one post detachably connectable to another side of the base portion opposite the one side which is connected to said container, said post being adapted to receive an artificial tooth structure.

11. An oral implant as claimed in claim 13 wherein said base portion is adapted to receive at least one post detachably connectable at one part to another side of the base portion opposite the one side which is connected to said container, and further including at least one cap detachably connected to the other side of the base portion at the one part of said base, so as to prevent the growth of bone over the part of said base which is adapted to receive said post.

12. An oral implant as claimed in claim 2 wherein said at least one shaft extends from at least one threaded aperture at the one side of said base portion, said threaded aperture extending completely through the base to the other side and providing access to the end of the shaft, the end of the shaft including means enabling the shaft to be rotated.

13. An oral implant for implanting an artificial tooth supporting structure in an opening created entirely within an edentulous span of the dental arch of the maxilla of a patient, such that the opening leaves sufficient bone to support said implant prior to being put in operation comprising:
  a basket-like container portion open at one side, said container portion having a size such that it can be passed easily into the opening;
  a base portion having a size such it can be wedged tightly in a portion of the opening in the bone; and
  adjusting means for adjusting the distance between said container portion and base portion, said adjusting means having two shafts projecting from one side of said base portion and connecting said base portion to the other side of said container portion, said shafts being rotatable and in threaded engagement with one of said container portion and base portion such that rotation of the shafts, adjust the distance between said base portion and container portion at the respective shaft, at least one of said base portion and container portion being pivotally connected to said shafts such that the container portion can be set at an angle to the base portion.

14. An oral implant as claimed in claim 13 wherein two blocks are pivotally attached to said container portion, said two shafts being in rotatable engagement with respective ones of said blocks, the other side of said container portion defining holes that allow the shafts to pass through and into engagement with said blocks.

15. An oral implant for implanting an artificial tooth supporting structure in an opening created entirely within an edentulous span of the dental arch of the maxilla of a patient, such that the opening leaves sufficient bone to support said implant prior to being put in operation, comprising:
  a basket-like container portion open at one side, said container portion having a size such that it can be passed easily into the opening;
  a base portion having a size such it can be wedged tightly in a portion of the opening in the bone; and
  adjusting means for adjusting the distance between said container portion and base portion, said adjusting means having at least one shaft projecting from one side of said base portion, said shaft connecting said base portion to another side of said container portion which is opposite the open side, said shaft being rotatable and in threaded engagement with one of said container portion and base portion such that rotation of the shaft adjusts the distance, and at least one post attached to another side of the base portion opposite the one side from which said shaft projects, said post being adapted to receive an artificial tooth supporting structure.

16. A method of reducing the maxillary sinus of a patient and installing an oral implant at an edentulous site along the dental arch adjacent to the sinus, comprising the steps of:
  forming an incision through the mucoperiosteal tissues at the edentulous site to expose any underlying maxillary bone of the dental arch mesial and distal to the sinus;
  creating an opening completely through the bone to expose a desired mesial-distal and bucco-platal opening of Schneiderian membrane at the floor of the sinus;

placing bone chips in an open side of a basketlike container portion of an oral implant, the container portion being connected at the side opposite the open side to a base portion by an adjusting means that can vary the spacing between the container portion and the base portion;

passing the container portion with the chips into the opening such that the bone chips are directed toward the Schneiderian membrane;

wedging the connected base portion into a portion of the opening at a sufficient depth to allow the tissue to cover it;

adjusting the adjusting means such that the bone chips in the container portion push against and lift the Schneiderian membrane so as to lift the sinus floor and shrink the size of the sinus; and closing the tissue over the implant.

17. A method as claimed in claim 16 further including the steps of:

reopening the tissue after a sufficient period of time has elapsed for new bone to grow in the dental arch so as to fill the groove and fuse with the bone chips;

attaching a post to the base of the implant at an attachment point such that said post projects beyond the bone and tissue;

suturing the tissue about the post; and attaching an artificial tooth structure to the post.

18. A method as claimed in claim 16 further including the step of placing bone chips in the opening prior to passing the container portion into the groove.

19. A method as claimed in claim 16 further including the step of placing bone chips in the opening between the container portion and the base portion prior to the step of passing the connected base portion into the opening.

20. A method as claimed in claim 17 wherein the implant is a submergible implant that is wedged in the opening such that no part of the base extends out of the opening, and further including the steps of placing a cap over the attachment point of the base portion prior to the step of closing the tissue, such that the growth of bone over the attachment point is prevented; and removing the cap after the step of reopening the tissue.

21. A method as claimed in claim 16 wherein the implant container is wider than the base and wherein the step of creating an opening involves making parts of the opening near both ends into a groove which is narrow enough for the base portion to be wedged therein, and making the center part wide enough for the container to easily pass therethrough.

22. A method as claimed in claim 16 wherein the implant container is narrower than the base and wherein the step of creating an opening involves making a groove that is narrow enough for the base portion to be gently wedged therein.

* * * * *